US009265457B2

United States Patent
Kudavelly et al.

(10) Patent No.: US 9,265,457 B2
(45) Date of Patent: Feb. 23, 2016

(54) APPARATUS AND METHOD FOR MEASURING A TISSUE ANALYTE SUCH AS BILIRUBIN USING THE BREWSTER'S ANGLE

(75) Inventors: Srinivas Rao Kudavelly, Bangalore (IN); Eduard Johannes Meijer, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 379 days.

(21) Appl. No.: 13/701,052

(22) PCT Filed: Apr. 28, 2011

(86) PCT No.: PCT/IB2011/051889
§ 371 (c)(1),
(2), (4) Date: Dec. 4, 2012

(87) PCT Pub. No.: WO2011/151744
PCT Pub. Date: Dec. 8, 2011

(65) Prior Publication Data
US 2013/0085351 A1    Apr. 4, 2013

Related U.S. Application Data

(60) Provisional application No. 61/351,053, filed on Jun. 3, 2010.

(51) Int. Cl.
*A61B 5/1455* (2006.01)
*A61B 5/00* (2006.01)
(Continued)

(52) U.S. Cl.
CPC .......... *A61B 5/14558* (2013.01); *A61B 5/0059* (2013.01); *A61B 5/14546* (2013.01);
(Continued)

(58) Field of Classification Search
CPC .......... A61B 5/14546; A61B 5/14558; A61B 5/1455
USPC .......................................... 600/310, 322, 315
See application file for complete search history.

(56) References Cited

U.S. PATENT DOCUMENTS 3,999,864 A    12/1976    Mutter
4,398,541 A     8/1983    Pugliese
(Continued)

FOREIGN PATENT DOCUMENTS

| JP | 2003194710 A | 7/2003 |
| WO | 9639925 | 12/1996 |
| WO | 2006073450 A2 | 7/2006 |

OTHER PUBLICATIONS

"Brewster's Angle"; Wikipedi; http://en.wikipedia.org/wiki/Brewster%27s_angle, pp. 1-4.
(Continued)

*Primary Examiner* — Eric Winakur

(57) ABSTRACT

A tissue analyte measuring device (2) includes a light source (4) structured to emit unpolarized light toward the skin surface of a subject, and a detector assembly (8) configured to receive light reflected from the skin surface of the subject and the transcutaneous tissues of the subject, the detector assembly including a polarizing filter (12) and a number of light detector subassemblies (14). The polarizing filter is structured to filter out s-polarized light and pass only p-polarized light to light detector subassemblies. The light source is structured and positioned to emit the unpolarized light in a manner wherein the unpolarized light will exit the measuring device at a predetermined angle with respect to a normal to a light emitting plane of the measuring device, wherein the predetermined angle is an angle (the Brewster's angle) at which only s-polarized light will be reflected by the skin surface when the unpolarized light is incident thereon.

17 Claims, 1 Drawing Sheet

(51) Int. Cl.
  *A61B 5/145* (2006.01)
  *G01N 21/21* (2006.01)
  *G01N 21/31* (2006.01)
  *G01N 21/47* (2006.01)

(52) U.S. Cl.
  CPC .............. *A61B5/441* (2013.01); *G01N 21/21* (2013.01); *G01N 21/31* (2013.01); *G01N 21/474* (2013.01); *A61B 2562/0242* (2013.01); *G01N 2021/215* (2013.01); *G01N 2021/3137* (2013.01)

(56) References Cited

U.S. PATENT DOCUMENTS

| | | | |
|---|---|---|---|
| 5,353,790 | A | 10/1994 | Jacques et al. |
| 6,847,835 | B1 | 1/2005 | Yamanishi |
| 6,882,873 | B2 | 4/2005 | Samuels et al. |
| 2007/0030482 | A1 | 2/2007 | Ji et al. |
| 2008/0219522 | A1 | 9/2008 | Hook |

OTHER PUBLICATIONS

Gregory J. Newman; "Bilirubin Measurements in Neonates", In-Vitro Diagnostic Instrumentation, Proceedings of SPIE, Vol. 3913, 2000, pp. 25-33.

Steven L. Jacques 1 et al; "Developing an Optical Fiber Reflectance Spectrometer to Monitor Bilirubinemia in Neonates", SPIE Proceedings vol. 2975, pp. 115-124, Laser-Tissue Interactions, San Jose, CA, Feb. 1997.

Guanhua et al, "Correction of Skyglint Above Water Surface Based on Polarized Principle", Advances in Water Science, vol. 18, No. 5, p. 762-767.

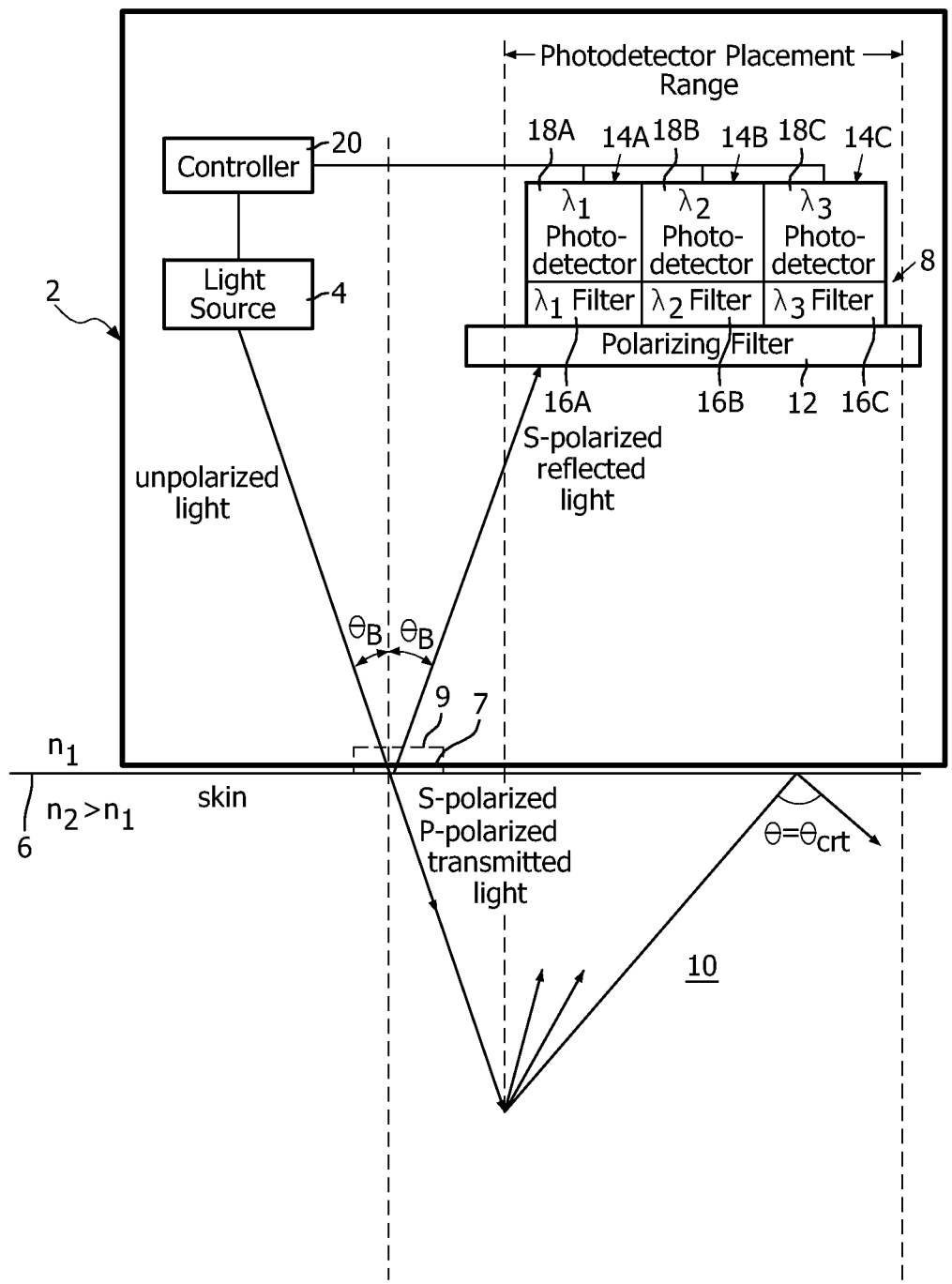

APPARATUS AND METHOD FOR MEASURING A TISSUE ANALYTE SUCH AS BILIRUBIN USING THE BREWSTER'S ANGLE

The present invention relates to measuring a tissue analyte, such as bilirubin, in individuals, such as neonates, and more specifically, to an apparatus and method of measuring a tissue analyte using the Brewster's angle. In one particular embodiment, the invention relates to an apparatus and method of determining transcutaneous bilirubin (TcB) and estimating total serum bilirubin (TSB) based thereon using the Brewster's angle.

Neonatal jaundice is a yellowing of the skin and other tissues of a newborn infant. Typically, a bilirubin level of more than 5 mg/dL manifests clinical jaundice in neonates. Management of jaundiced neonates typically requires the measurement and monitoring of total serum bilirubin (TSB), which is most commonly determined by analyzing a plasma or serum sample from the infant. However, as will be appreciated, the drawing of blood from infants for such an analysis causes pain and trauma. This fact has lead to the development of a number of non-invasive techniques for estimation of TSB.

One particular non-invasive method for estimation of TSB, known as Transcutaneous Bilirubinometry, involves measurement of transcutaneous bilirubin (TcB). The method relies on the high correlation between TcB and TSB. Transcutaneous Bilirubinometry devices work by directing light into the skin of the neonate and detecting specific wavelengths that are reflected back from the neonate's subcutaneous tissues. The number of wavelengths used varies among different devices. The detected optical signals are converted to electrical signals by a photodetector, such as a photodiode, and the electrical signals are analyzed by a controller to generate a TSB value based on the intensity of the reflected signals.

One problem with current Transcutaneous Bilirubinometry devices is the fact that they have no mechanism for overcoming the impact of reflections emanating from the surface of the skin. More specifically, as noted above, during transcutaneous estimation of bilirubin, a device needs to capture and analyze the light which penetrates the skin and is reflected back by the transcutaneous tissues of the subject. However, the incident light also undergoes a certain degree of reflection at the skin surface (without penetrating the skin). That reflected light is problematic because it often causes saturation of the detection device and/or adds bias to the intensity measurements. Similar problems exist for devices that use light to measure other tissue analytes, such as other blood or skin analytes.

Thus, there is room for improvement in the field of tissue analyte analysis using light, such as Transcutaneous Bilirubinometry. In particular, there is a need for a method and device that overcomes the adverse impact of light reflections emanating from the surface of the skin.

In one embodiment, a tissue analyte (such as bilirubin) measuring device is provided that includes a light source structured and positioned to emit unpolarized light toward a skin surface of a subject when the measuring device is positioned adjacent to the skin surface, and a detector assembly configured to receive light reflected from the subject including light reflected by the skin surface of the subject and by transcutaneous tissues of the subject, the detector assembly including a polarizing filter and a number of light detector subassemblies, the polarizing filter being structured to filter out s-polarized light and pass only p-polarized light to the number of light detector subassemblies. In the exemplary embodiment, the light source is structured and positioned to emit the unpolarized light in a manner wherein the unpolarized light will exit the measuring device at a predetermined angle with respect to a normal to a light emitting plane of the measuring device, the light emitting plane being configured to be positioned adjacent to a skin surface of a subject, wherein the predetermined angle is an angle (the Brewster's angle) at which only s-polarized light will be reflected by the skin surface when the unpolarized light is incident thereon.

In another embodiment, a method of measuring a tissue analyte of a subject, such as bilirubin, is provided that includes directing unpolarized light at the skin surface of a subject at a predetermined angle with respect to a normal to the skin surface, wherein in response to the unpolarized light being incident on the skin surface, reflected light is reflected by the skin surface and by transcutaneous tissues of the subject, filtering out s-polarized light from the reflected light and passing only p-polarized light from the reflected, and determining a measurement relating to the analyte based on the p-polarized light. In the exemplary embodiment, the predetermined angle is an angle at which only s-polarized light will be reflected by the skin surface (the Brewster's angle).

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various FIGURES. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

FIG. 1 is a schematic diagram of a bilirubin measuring device according to an exemplary embodiment of the present invention.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As employed, herein, the statement that two or more parts or components are "coupled" together shall mean that the parts are joined or operate together either directly or through one or more intermediate parts or components.

As employed herein, the statement that two or more parts or components "engage" one another shall mean that the parts exert a force against one another either directly or through one or more intermediate parts or components.

As employed herein, the term "number" shall mean one or an integer greater than one (i.e., a plurality).

The present invention relates the measurement of tissue analytes using light analysis, and in particular to an apparatus and method for measuring such tissue analytes. One such tissue analyte is bilirubin. For illustrative purposes, the present invention is described in connection with a device for measuring (e.g., estimating) bilirubin levels that is able to estimate bilirubin levels using Transcutaneous Bilirubinometry. It will be understood that that is meant to be exemplary, and that the present invention may be used to measure other tissue analytes, such as, without limitation, oxygen saturation ($SpO_2$), $VO_2$, melanin, and hemoglobin and hemoglobin components like methemoglobin, oxyhemoglobin, deoxyhemoglobin, carboxyhemoglobin, etc.

When light moves between two media of differing refractive indices, generally some of the light is reflected at the boundary and some of the light is transmitted through the boundary. At one particular angle of incidence, called the Brewster's angle ($\theta_B$), light with a particular polarization, identified below, cannot be reflected at the boundary, and instead is perfectly transmitted through the boundary. The Brewster's angle ($\theta_B$) is also known as the polarization angle. When traversing from a first medium with a refractive index $n_1$ to a second medium with a refractive index $n_2$, with $n_2 > n_1$, the Brewster's angle is given by: $\theta_B = \arctan(n_2/n_1)$.

The particular light polarization that cannot be reflected at the Brewster's angle is the polarization for which the electric field of the light waves lies in the same plane as the incident rays and the surface normal (i.e., the plane of incidence). This polarization is called p-polarization because it is parallel to the plane. On the other hand, light with perpendicular polarization is called s-polarized light. At the Brewster's angle, some s-polarized light will be transmitted through the boundary and some will be reflected. Thus, for light incident at the Brewster's angle on a boundary between two media where $n_2 > n_1$, any light that is reflected will be only s-polarized light.

As described in greater detail below, the present invention employs the properties of the Brewster's angle to provide a mechanism for overcoming the adverse impact of reflections emanating from the surface of the skin during the transcutaneous estimation of bilirubin levels.

FIG. 1 is a schematic diagram of a bilirubin measuring device 2 according to an exemplary embodiment of the present invention. Bilirubin measuring device 2 includes light source 4 which is structured to emit unpolarized light. Light source 4 may be a single light emitting device or a plurality of light emitting devices. Light source 4 may be, for example and without limitation, an LED (or LEDs) which emits/emit unpolarized light, such as unpolarized white light or unpolarized light of one or more particular wavelengths, or an incandescent light source (or sources) that emits/emit unpolarized light, such as unpolarized white light or unpolarized light of one or more particular wavelengths. In addition, as illustrated in FIG. 1, light source 4 is structured to direct the emitted unpolarized light toward skin surface 6 of a subject through light emitting plane 7 defined by light emitting portion 9 of bilirubin measuring device 2 so that it is incident against skin surface 6 at the Brewster's angle ($\theta_B$). The unpolarized light will thus be transmitted to/through a boundary between a first media through which the unpolarized light is originally transmitted, such as air [Is this correct?], having a refractive index $n_1$, and a second media comprising skin surface 6 having a refractive index $n_2$. As noted above, the Brewster's angle ($\theta_B$) may be determined using the equation $\theta_B = \arctan(n_2/n_1)$ (the refractive index of the skin is known in the literature). Alternatively, the Brewster's angle ($\theta_B$) may be determined empirically by adjusting the angular position of light source 4 and finding the angle at which p-polarized light disappears from the reflected light. Light source 4 may be structured to direct the emitted unpolarized light so that it is incident on skin surface 6 at the Brewster's angle ($\theta_B$) in a number of ways, such as by coupling a transmission optical fiber or fibers to light source 4 which directs the light at that angle (a collimating lens system may also be coupled to the fiber or fibers), or directing the light through a collimating lens system to direct the light at that angle. In addition, light emitting portion 9 may be a portion of a housing of bilirubin measuring device 2 that is structured to allow light to escape, and may be, for example, a hole or window (e.g., glass or plastic) in the housing that allows light to escape.

Bilirubin measuring device 2 further includes detector assembly 8 that is structured and configured to receive light reflected from the subcutaneous tissue 10 of a subject, such as a neonate. For example, one or more optical fibers may be coupled to detector assembly 8 to collect and direct the reflected light toward detector assembly 8. Detector assembly 8 is, in the exemplary embodiment, shielded from all light except the light that is reflected.

Detector assembly 8 includes polarizing filter 12. Polarizing filter 12 is a filter that passes only p-polarized light and filters out (i.e., rejects) s-polarized light. Detector assembly 8 also includes a number of detector subassemblies 14, which in the illustrated embodiment are detector subassemblies 14A, 14B, 14C (while three such detector subassemblies 14 are shown, that is meant to be exemplary only and it will be appreciated that more or less than three detector subassemblies 14 may also be used). Detector subassemblies 14A, 14B, 14C are each structured to receive and detect the light that is passed by polarizing filter 12 (i.e., p-polarized light only).

Each detector subassembly 14A, 14B, 14C includes an optical filter 16A, 16B, 16C operatively coupled to an associated photodetector 18A, 18B, 18C. Each photodetector 18A, 18B, 18C is a device, such as, without limitation, a photodiode, that converts light into a current or voltage. Furthermore, in the illustrated embodiment, each optical filter 16A, 16B, 16C is a band pass filter that is centered at a predetermined wavelength of light with a predetermined full-width at half maximum (FWHM). In the exemplary embodiment, the optical filter 16A, 16B, 16C are chosen to pass a plurality of predetermined wavelengths that are required for determining one or both of a TCB level and a TSB level of the subject (e.g., 484 nm, 517 nm, and 563 nm).

Bilirubin measuring device 2 also includes controller 20 that is operatively coupled to light source 4 and detector subassemblies 14A, 14B, 14C. Controller 20 includes a processing portion which may be, for example, a microprocessor, a microcontroller or some other suitable processing device, and a memory portion that may internal to the processing portion or operatively coupled to the processing portion and that provides a storage medium for data and software executable by the processing portion for controlling the operation of bilirubin measuring device 2, including calculating TcB and/or estimating TSB based on the intensity levels of the light detected by detector assemblies 14A, 14B, 14C.

In operation, bilirubin measuring device 2 is placed against skin surface 6 of a subject, such as a neonate. Controller 20 then causes light source 4 to emit and direct unpolarized light toward skin surface 6. As described elsewhere herein and as shown in FIG. 1, that light will be incident on skin surface 6 at the Brewster's angle ($\theta_B$). This will result in p-polarized light from the transmitted unpolarized light being perfectly transmitted through the boundary at skin surface 6, with no p-polarized light being reflected by skin surface 6. In addition, some s-polarized light from the transmitted unpolarized light will be transmitted through the boundary at skin surface 6 and some will be reflected by skin surface 6. Thus, the only light that will reflected by skin surface 6 is s-polarized light. That light will be filtered out by polarizing filter 12 and therefore not reach detector subassemblies 14A, 14B, 14C. As a result, no light reflected by skin surface 6 will be detected by detector subassemblies 14A, 14B, 14C and thus will not cause the adverse effects discussed elsewhere herein (e.g., saturation. Instead, only light that has penetrated skin surface 6 and has been reflected back will reach detector subassemblies 14A, 14B, 14C. More specifically, the p-polarized light perfectly transmitted through the boundary at skin surface 6 (along with any s-polarized light that is also transmitted) will undergo multiple scattering and some of it will be reflected by subcutaneous tissue 10 and be directed toward detector assembly 8. P-polarized light that is reflected from subcutaneous tissue 10 will be passed through polarizing filter 12 (any s-polarized light reflected from subcutaneous tissue 10 will be filtered out) and will be filtered by optical filters 16A, 16B, 16C and detected by photodetectors 18A, 18B, 18C, which each convert the detected light into an electrical signal (voltage or current). Those electrical signals are then provided to controller 20. In the exemplary embodiment, the electrical signals are amplified, for example using operational amplifiers, before being provided top controller 20. Controller 20 will then calculate TcB and/or estimate TSB based on those signals using any of a number of known methodologies. Suitable methodologies are described in, for example, one or more of the following, the disclosures of which are incorporated herein by reference: U.S. Pat. Nos. 5,353,790; 6,847,835; 6,882,873; S. L. Jacques et al., "Developing an Optical Fiber reflectance Spectrometer to Monitor Bilirubinemia in Neonates", SPIE Proceedings 2975:115-124, *Laser-Tissue Interactions*, San Jose, Calif. February 1997; and G. J. Newman, "Bilirubin Measurements in Neonates," SPIE Vol. 3913 (2000), in *In Vitro Diagnostic Instrumentation*.

In one exemplary embodiment, bilirubin measuring device 2 is a fully integrated system, where both light source 4 and detector assembly 8 are positioned on the same measurement board, positioned slightly apart from the skin or measurement surface, to allow the light emitted by light source 4 to be reflected and detected as described herein. Care should be taken to prevent direct light from light source 4 from hitting detector assembly 8. Rather, only reflected light should be permitted to do so.

Furthermore, the optimal placement of the detector subassemblies 14A, 14B, 14C (as well as polarizing filter 12) could be estimated/predicted based on two parameters, the angle of the s-polarized reflected light (which, as shown in FIG. 1 is same as the Brewster's angle ($\theta_B$) of the incident light) and the depth of penetration within the skin of the incident light. The light which penetrates skin surface 6 depends on the intensity of the incident light which could penetrate till the end of the epidermis (below skin surface 6, where the bilirubin is deposited). The light which has penetrated skin surface 6 undergoes multiple scatterings and also total internal reflection. If the scattered light incident angle is less than $\theta_{crt}$ (critical angle), then the light will be reflected back. So, in the exemplary embodiment, the detector subassemblies 14A, 14B, 14C should not be placed beyond the $\theta_{crt}$ (critical angle), since no reflected light from the skin is available. In another alternative embodiment, the detector signal is scanned as a function of angle to estimate the angle range over which the light is transmitted back from skin so that an outer boundary can be established where there is determined to be no light transmitted back.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A tissue analyte measuring device (2), comprising:
a light source (4) structured and positioned to emit unpolarized light toward a skin surface (6) of a subject at a predetermined angle at which only s-polarized light will be reflected by the skin surface when the measuring device is positioned adjacent to the skin surface;
a detector assembly (8) configured to receive light reflected from the subject including light reflected by the skin surface of the subject and by transcutaneous tissues of the subject, the detector assembly including a polarizing filter (12) and a number of light detector subassemblies (14), the polarizing filter being structured to filter out s-polarized light and pass only p-polarized light to the number of light detector subassemblies; and
one or more physical computer processors configured by computer readable instructions to control the light source and the detector assembly and to compute a measurement relating to the analyte from the measured p-polarized light.

2. The measuring device according to claim 1, wherein the light source is structured and positioned to emit the unpolarized light in a manner wherein the unpolarized light will exit the measuring device at the predetermined angle with respect to a normal to a light emitting plane (7) of the measuring device, the light emitting plane being configured to be positioned adjacent to a skin surface of a subject.

3. The measuring device according to claim 2, wherein the predetermined angle is a Brewster's angle determined using a refractive index of human skin.

4. The measuring device according to claim 2, wherein the light source is structured and positioned to emit the unpolarized light in a manner wherein the unpolarized light will exit the measuring device and be incident on the skin surface at a predetermined angle with respect to a normal to the skin surface when the measuring device is placed against the skin surface.

5. The measuring device according to claim 4, wherein the predetermined angle is a Brewster's angle determined using a refractive index of human skin.

6. The measuring device according to claim 1, wherein a number of light detector assemblies is a plurality of light detector assemblies.

7. The measuring device according to claim 6, wherein each of the light detector subassemblies includes a filter (16) and a photodetector (18).

8. The measuring device according to claim 7, wherein each filter is centered at a predetermined wavelength.

9. The measuring device according to claim 8, wherein the tissue analyte is bilirubin, wherein the filters are structured to pass a plurality of predetermined wavelengths required for determining one or both of a TCB level and a TSB level of the subject.

10. The measuring device according to claim 9, wherein the one or more physical computer processors comprises a controller (20) operatively coupled to the light source and the number of light detector subassemblies, wherein each photodetector is structured to convert light received thereby to an electrical signal, and wherein the controller is adapted to determine one or both of a TCB level and a TSB level of the subject based on the electrical signal received from each photodetector.

11. The measuring device according to claim 7, wherein each photodetector is a photodiode.

12. A method of measuring a tissue analyte of a subject, the method being implemented in a computer system including one or more physical processors and storage media storing machine-readable instructions, the method comprising:

directing unpolarized light at a skin surface of a subject at a predetermined angle with respect to a normal to the skin surface, wherein in response to the unpolarized light being incident on the skin surface, reflected light is reflected by the skin surface, comprising only s-polarized light, and by transcutaneous tissues of the subject;

filtering out s-polarized light from the reflected light and passing only p-polarized light from the reflected light; and determining a measurement relating to the analyte based on the p-polarized light.

13. The method according to claim 12, wherein the predetermined angle is an angle at which only s-polarized light will be reflected by the skin surface.

14. The method according to claim 12, wherein the predetermined angle is a Brewster's angle determined using a refractive index of human skin.

15. The method according to claim 12, wherein the determining includes filtering the p-polarized light to produce one or more filtered lights, detecting the one or more filtered lights and determining the measurement using the detected one or more filtered lights.

16. The method according to claim 15, wherein the one or more filtered lights is a plurality of filtered lights each including a predetermined wavelength.

17. The method according to claim 16, wherein the tissue analyte is bilirubin, and wherein each predetermined wavelength is required for determining one or both of a TCB level and a TSB level of the subject.

* * * * *